United States Patent [19]

Asinger et al.

[11] 4,028,406

[45] June 7, 1977

[54] PROCESS OF PREPARING PENICILLAMINE

[75] Inventors: Friedrich Asinger, Aachen; Heribert Offermanns, Grossauheim; Karl-Heinz Gluzek, Aachen, all of Germany

[73] Assignee: Deutsche Gold- und Silber-Scheideanstalt vormals Roessler, Frankfurt, Germany

[22] Filed: Feb. 13, 1976

[21] Appl. No.: 657,835

Related U.S. Application Data

[63] Continuation of Ser. No. 481,858, June 21, 1974, abandoned, which is a continuation of Ser. No. 158,512, June 30, 1971, abandoned.

[30] Foreign Application Priority Data

July 3, 1970 Germany ........................... 2032952
May 11, 1971 Germany ........................... 2123232

[52] U.S. Cl. .................... 260/534 S; 260/306.7 C; 424/269; 426/807
[51] Int. Cl.$^2$ ......................................... C07C 99/00
[58] Field of Search ................................. 260/534 S

[56] References Cited

FOREIGN PATENTS OR APPLICATIONS 738,520   9/1969   Belgium ...................... 260/534 S

OTHER PUBLICATIONS

Wagner et al., "Synthetic Organic Chemistry", (1953), pp. 412, 413, 570.
Asinger et al., Annual Report of Landesamt fur Forschung des Landes of Nordrhein–Westfalen, (1967), pp. 11–35.

Primary Examiner—Joseph E. Evans
Attorney, Agent, or Firm—Cushman, Darby & Cushman

[57] ABSTRACT

Improvements in the process of preparing penicillamine or a homolog thereof by reacting an α-carbon atom branched aldehyde, sulfur and ammonia to form a thiazoline-$\Delta^3$, reacting the thiazoline-$\Delta^3$ with anhydrous hydrogen cyanide to form a thiazolidine-4-carbonitrile, hydrolyzing the nitrile to form a mixture of the salt of the thiazolidine-4-carboxylic acid and ammonium salts, separating off the ammonium salts and hydrolytically decomposing the thiazolidine-4-carboxylic acid, wherein under the action of a mineral acid the thiazolidine-4-carbonitrile is in the first stage converted at low temperatures into the salt of the thiazolidine-4-carbonamide and then at higher temperatures converted into the salt of the thiazolidine-4-carboxylic acid.

14 Claims, No Drawings

PROCESS OF PREPARING PENICILLAMINE

This is a continuation of application Ser. No. 481,858, filed June 21, 1976 which in turn is a continuation of application Ser. No. 158,512 filed June 30, 1971 both now abandoned.

BACKGROUND OF THE INVENTION

This invention relates to a process for preparing penicillamine or its homologs on the basis of α-carbon atom branched aliphatic aldehydes, sulfur, ammonia and hydrogen cyanide.

A process of preparing pencillamine is already known in which isobutyraldehyde is reacted with sulfur and ammonia to form 2-isopropyl-5,5-dimethyl-thiazoline-$\Delta^3$, which is then converted by reaction with hydrogen cyanide into 2-isopropyl-5,5-dimethyl-thiazolidine-4-carbonitrile, the nitrile hydrolyzed under exclusion of oxygen with hydrochloric acid at a temperature of between 70° and 100° C to form 2-isopropyl-5,5-dimethyl-thiazolidine-4-carboxylic acid-hydrochloride and this through further hydrolytic decomposition converted into penicillamine-hydrochloride (BEPS 738,520). The disadvantage of this process is that the hydrolysis of the nitrile to the carboxylic acid provides only moderate yields of the acid.

SUMMARY OF THE INVENTION

In accordance with the invention, an improved process has now been found for preparing penicillamine and its homologs by reacting an α-carbon atom branched aliphatic aldehyde with sulfur and ammonia to form a thiazoline-$\Delta^3$, converting the thiazoline-$\Delta^3$ with anhydrous hydrogen cyanide into the thiazolidine-4-carbonitrile, hydrolyzing the nitrile to form the salt of the thiazolidine-4-carboxylic acid and ammonium salts and hydrolytically decomposing the thiazolidine-4-carboxylic acid to form the penicillamine or its homologs which comprises hydrolyzing the thiazolidine-4-carbonitrile with a mineral acid in a first stage at a low temperature to form the salt of the thiazolidine-4-carbonamide and thereafter in a second stage hydrolyzing the carbonamide at high temperatures whereby the salt of the thiazolidine-4-carboxylic acid is formed.

According to the process of the invention, the stagewise hydrolysis of the thiazolidine-4-carbonitrile to the thiazolidine-4-carboxylic acid takes place with very high yields of the desired acid and with correspondingly high yields of the penicillamine or its homologs thereafter being obtained. The so obtained products are of higher purity than those prepared by known processes.

The process is advantageously used for the manufacture of penicillamine, i.e. α-amino-62-mercapto-isovalerianic acid. This product has proved particularly useful as a food supplement for example, for feeding chicks and other fowl and as a medicament for use in treating Wilson's disease or cystinuria in humans.

DESCRIPTION OF THE INVENTION

In order to form the thiazoline-$\Delta^3$, a mixture preferably of stoichiometric amounts of aldehyde and sulfur with an excess amount of ammonia, advantageously in the presence of an amine is heated to 50°–100° C. The water formed in the reaction is advantageously taken off with the help of an entraining agent which forms with the water an azeotropic mixture. Any entrained aldehyde can be reintroduced into the reaction mixture. The thiazoline-$\Delta^3$ is recovered from the reaction mixture in pure form by distillation under reduced pressure under exclusion of air.

As aldehydes, there can be used any aliphatic aldehyde branched at the α-carbon atom. Isobutyraldehyde for instance forms penicillamine and α-methylbutyraldehyde, homopenicillamine. Instead of using sulfur in its elementary form, the latter being the preferable form, there can also be used compounds which under the reaction conditions split off sulfur, such as polysulfides, or compounds of the type of 7-phenyl-7-alkyl-amino-8-thioxo-1,2,3,4,5,6-hexathiocanes. The ammonia is preferably used in gaseous form. Instead of ammonia there can also be used different solutions of ($NH_4NO_3 \cdot 2NH_3$). As amines, there are particularly suitable the secondary and tertiary amines and especially the water immiscible amines whose boiling point lies between about 40° and about 150° C, such as for instance trialkylamine, for example triethylamine or heterocyclic amines, such as pyridine. For each mole of aldehyde, 0.1–0.5 mols of amine are used. As entraining agent for the water formed in the reaction there can be used for instance benzene, cyclohexane or a chlorinated hydrocarbon such as tetrachloromethane or even the aldehyde itself can be used for this purpose.

For forming the thiazolidine-4-carbonitrile, the thiazoline-$\Delta^3$ is treated with an about excess amount, but preferably with an about stoichiometric amount of hydrogen cyanide. For example the thiazoline-$\Delta^3$ dissolved in an organic solvent, for instance an alkanol such as methanol, an ether such as diethylether, and aliphatic or aromatic hydrocarbon such as light gasoline, or a halogenated hydrocarbon such as tetrachloromethane, is first reacted with the hydrogen cyanide at temperatures lower than 10° C and then after reacted at room temperature. The thiazolidine-4-carbonitrile is separated out from the resulting reaction mixture by cooling the mixture to temperatures of lower than −30° C or alternatively by subjecting the mixture to an inert gas stream or to reduced pressures for removing the solvent and the excess hydrogen cyanide. The thusly produced nitrile can in general be directly introduced into the hydrolysis step. If necessary, it can be purified for instance by precipitating the same out of a hydrocarbon. If the preparation of the nitrile is carried out in an alkanol as solvent, then the reaction mixture can be directly introduced into the hydrolysis, the separation of the nitrile being superfluous in this case.

In accordance with the invention, the thiazolidine-4-carbonitrile is hydrolyzed in two stages to form the thiazolidine-4-carboxylic acid. The conversion takes place under the action of an aqueous mineral acid. In this connection, strong mineral acids are involved which are capable of bringing about the hydrolysis but which do not at the same time bring about a destruction of the thiazolidine compounds. Examples of suitable acids are sulfuric acid, the hydrogen halides or their mixtures, hydrochloric acid being preferred. These are used in at least stoichiometric amounts calculated with respect to the nitrile.

The hydrolysis is carried out in the first stage to form the mineral acid salt of the thiazolidine-4-carbonamide. The hydrolysis is advantageously carried out in the presence of an organic solvent, preferably an alkanol such as for instance methanol, at a temperature of from 0° to 80° C. The reaction is preferably started at temperatures of from 0 to 20° C and as the reaction proceeds the temperature is slowly increased for instance up to 50° C and preferably up to 80° C.

In the second stage, the salt of thiazolidine-4-carbonamide is converted into the salt of the thiazolidine-4-carboxylic acid. In this stage, the carbonamide in the mineral acid, after driving off the solvent which was used in the first stage, is heated up to 80°–150° C.

In accordance with a preferred mode of carrying out the process of the invention where hydrogen chloride is used as the acid, the thiazolidine-4-carbonitrile is either a. suspended in concentrated hydrochloric acid or preferably b. dissolved in a lower alcohol for instance methanol.

When the mixture corresponding to a) is used the hydrolysis is carried out under stirring at room temperature. For each mol of nitrile, at least about 200 ml and preferably between about 400–1000 ml concentrated hydrochloric acid is used. When the solution corresponding to b) is used, the hydrolysis is started at temperatures of 0°–20° C and in the further course of the reaction increased to about 50° C and preferably to 80° C most advantageously to between about 50 and 65° C, the hydrolysis being carried out in the presence of an about stoichiometric amount of water calculated on the nitrile by passing gaseous hydrochloric acid through the mixture. For each mol of nitrile, in general about 100 to 1000 ml alkanol are used. The thiazolidine-4-carbonamide-hydrochloride which separates out is filtered off, washed if necessary with a solvent, preferably acetone, and if necessary evaporated to dryness and then taken up, using hydrochloric acid so that calculated on the carbonamide more than the stoichiometrically necessary amount of water is present.

The thiazolidine-4-carbonamide-hydrochloride which is formed either from a) or b) is for further hydrolysis treated with the hydrochloric acid at temperatures of about 100° C. Advantageously for this purpose, a mixture is heated to boiling under reflux, so that temperatures of about 105° C are obtained. Preferably the concentration of the hydrochloric acid is 10–15% by weight and for each mol of carbonamide, 300–3000 ml, preferably 1000–2000 ml are present. Hydrochloric acid is preferably used for carrying out the hydrolysis of 2-isopropyl-5,5-dimethyl-thiazolidine-4-carbonitrile by the procedure just described.

Following the hydrolysis of the thiazolidine-4-carbonitrile, a reaction mixture is obtained containing the thiazolidine-4-carboxylic acid as a salt with the mineral acid and also ammonium salts. For working up these mixture and for converting the salts of the thiazolidine-4-carboxylic acid into penicillamine or its homologs, it is necessary to separate out the ammonium salts, neutralize the mineral acids and hydrolytically decompose the ring compounds by means of a steam distillation. This process can be carried out by various methods and using different sequences:

1. The reaction mixture is directly reacted with an alkaline acting substance such as an alkali carbonate, -bicarbonate or -hydroxide, and preferably with soda lye, so that the salt of the thiazolidine-4-carboxylic acid is converted into the free thiazolidine-4-carboxylic acid. Sufficient water is then added so that the ammonium salts and the superfluous salts are dissolved, the thiazolidine-4-carboxylic acid, however, remaining undissolved. The latter is then filtered off and subjected to a steam distillation.

2. The reaction mixture is preferably under reduced pressure brought to dryness. This process is suitable so far as the mineral acids present in the reaction mixture do not bring about a decomposition of the carboxylic acids. Advantageously the process is used when hydrochloric acid is present as mineral acid. The residue is reacted with an anhydrous lower alkanol containing up to 5 carbon atoms and preferably with n-propanol, and the thiazolidine-4-carboxylic acid as the salt is then in a conventional manner for instance through heating in the presence of an acid catalyst such as sulfuric acid or hydrochloric acid converted into the thiazolidine-4-carboxylic acid ester. The resulting mixture in which the ester is present as a salt is neutralized with an alkaline acting substance such as an amine, alkali acetate, alkali carbonate or bicarbonate or hydroxide and preferably with soda lye to form the free ester. The latter is extracted with an organic solvent such as a hydrocarbon, halogenated hydrocarbon or ether, distilled under reduced pressure and subjected to steam distillation in the presence of a mineral acid. 3) As set out in 2) above, the reaction mixture is reduced to dryness and subjected to a steam distillation. The residue is then evaporated to dryness and extracted either with an alkanol such as methanol or ethanol or preferably with a water-miscible liquid carbonyl compound and most preferably with acetone. In the case of the use of a carbonyl compound, the residue is hot extracted, if necessary after boiling up the residue in the carbonyl compound and the extract following evaporating off of the carbonyl compound boiled out with water. 4) As set out above in 2), the reaction mixture is brought to dryness and boiled up with a water-miscible liquid carbonyl compound preferably acetone. After cooling, the solid material is filtered off and recovered and further worked up in one of the following manners:

The filtered off solids are either hot extracted with a carbonyl compound and the extract subjected to a steam distillation, or the solids are first subject to a steam distillation and then worked up as set out in 3), or the solids are directly extracted with an anhydrous alkanol such as methanol or ethanol and the extract subjected to a steam distillation.

The aforesaid described methods of proceeding for working up the carboxylic acids can in case it is necessary be interlinked in a suitable manner. The steam distillation if necessary can be carried out in the presence of a small amount of a mineral acid for instance hydrochloric acid. There is advantageously used for the extraction a Soxhlet apparatus.

The penicillamine or a homolog thereof which is precipitated out as its salt with hydrochloric acid or other acid is converted into the free acid in the conventional manner for instance by treatment with alkali lye or bicarbonate or by means of appropriate ion exchangers. In carrying out the process of the invention in the steps where penicillamine or its homologs or salts are present, access of air can be prevented by means of an inert gas such as nitrogen. The splitting up of the racemate as final product can take place according to the known methods for instance according to the Brucin method.

In a variation of the process described above, the salts of the thiazolidine-4-carbonamide, which have been received by hydrolysis of the thiazolidine-4-carbonitrile, can be directly converted into the salts of penicillamine amide or a homolog thereof by a steam distillation, which avoids the step of forming the thiazolidine-4-carboxylic acid. The salts of penicillamine amide or a homolog thereof is then converted into the salt of penicillamine or its homolog by subjecting the same to a hydrolysis with a mineral acid using the same method as is used for converting the thiazolidine-4-carbonamide into the thiazolidine-4-carboxylic acid, however, the conversion is carried out under an inert gas as for instance nitrogen.

The working up of the reaction mixture containing penicillamine or its homologs and ammonium salts formed in the hydrolysis for effecting the separation of the ammonium salts can be carried out analogously to the aforedescribed process for separating the ammonium salts from the thiazolidine-4-carboxylic acids. For example, the reaction mixture can be evaporated to dryness and the residue extracted with an alkanol such as methanol or ethanol or advantageously with a water-miscible liquid carbonyl compound and preferably with acetone. In the case where a carbonyl compound is used the extraction is a hot extraction and advantageously after boiling out the residue with the carbonyl compound and following evaporating off of the carbonyl compound, the residue is also boiled out with water.

The process of this invention is preferably applicable to the production of penicillamine i.e.

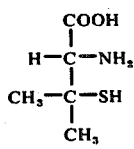

Homologs of penicillamine which are within the scope of this invention are those in which one or two of the $CH_3$-groups within the above formula are replaced by one or two alkylgroups having 2 to 4 C-atoms. The alkylgroup can be the same or different.

The following examples are included to further illustrate the present invention and are not intended to be a limitation thereof.

EXAMPLE 1

A mixture of 1442 g (20 mol) freshly distilled isobutyraldehyde substantially free of trimericisobutyraldehyde, 101 g (1 mol) triethylamine and 320 g (10 mol) sulfur was treated with gaseous ammonia. The resulting mixture was maintained at the boiling temperature thereof and the water of reaction removed azeotropically. The reaction took 7 hours for completion. In this period 400 ml water were removed. Following distillation under reduced pressure of 20 Torr, there were recovered from the mixture 1247 g 2-isopropyl-5,5-dimethyl-thiazoline-$\Delta^3$ corresponding to a yield of 79%.

In a vessel provided with a reflux cooler, which was fed with cooling fluid having a temperature of $-15°$ C, a mixture of 1573 g (10 mol) of 2-isopropyl-5,5-dimethylthiazoline-$\Delta^3$ and 1000 ml methanol were over a 2 hour period treated with 300 g (11 mol) gaseous hydrogencyanide. The temperature of the reaction mixture was maintained at 5° C by cooling. At the end of the gas treatment, the mixture without further cooling was allowed to stand for 4 hours. Thereafter the methanol and the excess hydrogencyanide were driven off under reduced pressure.

The thusly obtained crude nitrile was, under cooling, slowly reacted with concentrated hydrochloric acid. The resulting mixture was allowed to stand under stirring at room temperature for 2 days, thereafter refluxed for 2 days at the boiling temperature thereof (105° C) and finally evaporated to dryness. The residue was reacted with 2000 ml acetone, briefly boiled, cooled and filtered. The thusly recovered yellow colored solid substance contained about 285 g ammonium chloride, 1285 g 2-isopropyl-5,5-dimethylthiazolidine-4-carboxylic acid-hydrochloride, corresponding to a 53% yield referred to the charged thiazoline.

59 g of the recovered solid (carboxylic acid-hydrogen chloride content 0.2 mol) were dissolved in 100 ml hot water and a hot solution of 10.6 g sodium carbonate in 20 ml water introduced therein. The free 2-isopropyl-5,5-dimethylthiazolidine-4-carboxylic acid thereby formed was thereby precipitated out. Any adhering residue of inorganic salt was removed by boiling with water. The carboxylic acid had a melting point (decomposition point) of 181°–183° C. The yield amounted to 36.5 g, corresponding to a yield of 90% calculated on the charged 2-isopropyl-5,5-dimethyl-thiazolidine-4-carboxylic acid-hydrochloride.

40.6 g (0.2 mol) 2-isopropyl-5,5-dimethyl-thiazolidine-4-carboxylic acid were subjected to steam distillation under nitrogen for sufficient time that no further isobutyraldehyde passed over. The distillation residue was then evaporated to dryness under reduced pressure and further dried over diphosphorus pentoxide. There remained 28.6 g pure dl-penicillamine corresponding to a 69% yield calculated on the thiazolidine-4-carboxylic acid. The dl-penicillamine had a melting point (decomposition point) of 201°–202° C.

EXAMPLE 2

The procedure of Example 1 was followed, however 59 g of the compound recovered from the hydrolysis of the nitrile (0.2 mol content of 2-isopropyl-5,5-dimethyl-thiazolidine-4-carboxylic acid-hydrochloride) were reacted with 500 ml anhydrous n-propanol, 5g concentrated sulfuric acid and 50 ml benzene. The mixture was maintained at the boiling temperature for 2 days. The water which was formed in the reaction was taken off as an azeotropic mixture. The reaction mixture following removal of the alcohol was neutralized with sodium carbonate solution until a blue color was obtained and it was then extracted 3 times using for each extraction 100 ml diethyl ether. The extract was dried with calcium chloride and following evaporation of the solvent the ester was distilled off under reduced pressure. There were recovered 30.4 g of 2-isopropyl-5,5-dimethyl-thiazolidine-4-carboxylic acid-n-propylester which had a boiling point of 83° C at 0.1 Torr. The yield amounted to 62% calculated on the charged thiazolidine-4-carboxlyic acid-hydrochloride. 49 g (0.2 mol) of the ester were reacted with 100 ml concentrated hydrochloric acid and 300 ml water and the resulting mixture subjected to steam distillation under a nitrogen atmosphere until no further isobutyraldehyde passed over. The distillation residue was evaporated to dryness under reduced pressure and further dried over phosphorus pentoxide. The yield amounted to 35 g of dl-penicillamine hydrochloride corresponding to 94% calculated on the charged thiazolidine-4-carboxylic ester.

EXAMPLE 3

Example 1 was repeated, however, 59 g of the substance recovered from the hydrolysis of the nitrile (0.2 mol content of 2-isopropyl-5,5-dimethyl-thiazolidine- 4-carboxylic acid-hydrogen chloride) was taken up under warming in 100 ml anhydrous methanol. After cooling, the undissolved ammonium chloride (9.8g) was filtered off. The solution was evaporated under reduced pressure. The residue was washed with acetone. There remained 44 g 2-isopropyl-5,5-dimethyl-thiazolidine-4-carboxylic acidhydrogen chloride containing 0.4% of ammonium chloride. The yield of pure carboxylic acid-hydrochloride amounted to 92% of the crude charged carboxylic acid-hydrogen chloride.

48 g (0.2 mol) 2-isopropyl-5,5-dimethyl-thiazolidine-4-carboxylic acid-hydrochloride were, under nitrogen, subjected to a steam distillation until no further isobutyraldehyde passed over. The distillation residue was evaporated to dryness under reduced pressure. There remained 35.4 g of a solid substance consisting of 99.5% dl-penicillamine-hydrogen chloride and 0.5% of ammonium chloride, corresponding to a 95% yield of dl-penicillaminehydrogen chloride calculated on the charged thiazolidine-4-carboxylic acid-hydrochloride.

EXAMPLE 4

Example 1 was repeated, however, the crude nitrile was dissolved in 5000 ml methanol. The resulting solution after addition of 300 ml concentrated hydrochloric acid was treated with gaseous hydrogen chloride for 3 days. The temperature for the first 6 hours was maintained through cooling at 5° C. In the further course of the reaction without cooling a temperature of 35°–45° C set in. The separated thiazolidine-4-carbonamide-hydrochloride was filtered off and the remaining filtrate evaporated to dryness under reduced pressure. The residue was washed with 2000 ml acetone. A total of 2125 g 2-isopropyl-5,5-dimethyl-thiazolidine-4-carbonamide-hydrochloride was recovered corresponding to a yield of 89% calculated on the charged thiazoline. The melting point (decomposition point) of the 2-isopropyl-5,5-dimethyl-thiazolidine-4-carbonamide hydrochloride amounted to 240°–242° C.

2124 g (8.9 mol) 2-Isopropyl-5,5-dimethyl-thiazolidine-4-carbonamide-hydrochloride were dissolved in a mixture of 1000 ml water and 3000 ml concentrated hydrochloric acid and this solution maintained for 40 hours under reflux at the boiling temperature (105°C). A substantial part of the reaction product was separated out on cooling of the solution. The separated material was filtered off and the filtrate evaporated to dryness under reduced pressure. The crude product which was recovered was purified and washed with 3000 ml acetone. The thereby decolored product contained 450 g ammonium chloride, 2015 g 2-isopropyl-5,5-dimethyl-thiazolidine-4-carboxylic acid-hydrochloride corresponding to a yield of 84calculated on 2-isopropyl-5,5-dimethyl-thiazoline-$\Delta^3$ and had a melting point (decomposition point) of 211°–213° C. The further working up of the product corresponded to that set out in Example 1.

EXAMPLE 5

92.1 g (0.5 mol) 2-isopropyl-5,5-dimethyl-thiazolidine-4-carbonitrile were stirred together with 96 g concentrated sulfuric acid. Thereafter further 96 g of concentrated sulfuric acid which had been diluted with 18 g water were added dropwise to the mixture. The mixture was stirred first for 12 hours at about 15° C and then for a further 4 hours at 60° C. The reaction mixture was then poured into ice, neutralized with sodium carbonate and extracted with diethyl ether. The ether extract was evaporated to dryness. As residue there remained 59 g 2-isopropyl-5,5-dimethylthiazolidine-4-carbonamide which corresponded to a yield of 59% calculated on the charged nitrile. The carbonamide had a melting point of 86°–87° C.

EXAMPLE 6

47.8 (0.2 mol) 2-Isopropyl-5,5-dimethyl-thiazolidine-4-carbonamide-hydrochloride prepared according to Example 4 were dissolved in 500 ml water and under nitrogen subjected to steam distillation until no further isobutyraldehyde passed over. The residue was then evaporated to dryness under nitrogen and at reduced pressure. The dry residue was taken up to 100 ml of methanol. Through the addition of 100 ml diethylether, the penicillamine-amidehydrogen chloride was precipitated out. The yield amounted to 35.8 g corresponding to 97% calculated on the charged thiazolidine-carbonamide-hydrochloride. The penicillamine-amide-hydrochloride had a melting point (decomposition point) of 233°–235° C.

18.5 g (0.1 mol) Penicillamineamide-hydrochloride was introduced into 100 ml concentrated hydrochloric acid. The mixture was maintained under reflux at the boiling temperature for 40 hours, then cooled, and brought to dryness under reduced pressure. All of the processing steps were carried out under nitrogen. A mixture of 4.6 g ammonium chloride and 16.1 g penacillamine-hydrochloride was recovered. The yield of penicillamine-hydrochloride amounted to 87% calculated on the penicillamine-amide-hydrochloride. The ammonium chloride was separated from the penicillamine-hydrochloride by extraction with ethanol.

EXAMPLE 7

23.9 g (0.1 mol) Carbonamide-hydrochloride obtained by hydrolysis of 2-isopropyl-5,5-dimethyl-thiazolidine-4-carbonitrile in the presence of hydrochloric acid was further hydrolyzed by subjecting the same to steam distillation. After 6 l of distillate had passed over the distillation residue was evaporated to dryness under reduced pressure. The recovered penicillamine-amide-hydrogen chloride was taken up in 50 ml concentrated aqueous hydrochloric acid and 100 ml water and the mixture kept at the boiling point for 4 hours. The mixture was thereafter evaporated to dryness under reduced pressure. The residue was boiled out in acetone, freed from the acetone by filtration and then boiled out for ½ hour in 100 ml water. Thereafter the residue was evaporated to dryness under decreased pressure whereby a mixture of penicillamine-hydrochloride and ammonium chloride separated out. This mixture was taken up in 100 ml anhydrous ethanol. An ammonium chloride which was still present in undissolved form was separated off by filtering. The pH of the remaining filtrate was then adjusted to a value of between 5 and 6 by addition of triethylamine dissolved in ethanol. After a short time, the penicillamine separated out. The yield of penicillamine amounted to 13.0 g corresponding to 88% calculated on the charged carbonamide-hydrochloride. The penicillamine had a melting point of 212° C.

EXAMPLE 8

The 2-isopropyl-5,5-dimethyl-thiazolidine-4-carbonitrile obtained by reacting 787 g (5 mol) 2-isopropyl-5,5-dimethylthiazoline-$\Delta^3$ with 270 g (10 mol) hydrogen cyanide in the conventional matter was taken up to 2000 ml methanol. The resulting solution was reacted with 150 ml concentrated aqueous hydrochloric acid and treated with gaseous hydrogen chloride. The temperature of the solution at first amounted to 15° C but was increased in a short time to 65° C so that the solution was brought to boiling. The introduction of hydrogen chloride gas took place for 2 hours. Thereafter the solution was allowed to stand for 5 hours under stirring whereby 2-isopropyl-5,5-dimethyl-thiazolidine-4-carbonamide-hydrochloride separated out in the form of crystals. The crystals were filtered off and washed with acetone. By evaporating the mother liquor, a further quantity of carbonamide-hydrochloride was recovered. The latter was also washed with acetone. The total yield of carbonamide hydrochloride amounted to 1035 g. Calculated on the charged thiazoline, this amounted to a yield of 90%. the carbonamide-hydrochloride had a melting point (decomposition point) of 240°–242° C.

239 g (1 mol) Of the thusly recovered 2-isopropyl-5,5-dimethyl-thiazolidine-4-carbonamide-hydrochloride were taken up in a mixture of 500 ml concentrated aqueous hydrochloric acid and 1000 ml water. The solution was maintained at the boiling temperature (about 105° C) for 4 hours, then cooled and evaporated to dryness under reduced pressure. The product recovered contained 214 g 2-isopropyl-5,5-dimethyl-thiazolidine-4-carboxylic acid-hydrochloride, corresponding to an 89% yield calculated on the charged carbonamide-hydrogen chloride. IR-spectroscopic analysis of the product could not establish any carbonamide-hydrochloride therein. The further working up to penicillamine was carried out in the usual manner.

EXAMPLE 9

2-Isopropyl-5,5-dimethyl-thiazolidine-4-carbonitrile obtained in the usual manner by reacting 787 g (5 mol) 2-isopropyl-5,5-dimethyl-thiazoline-$\Delta^3$ with 438 g (10 mol) hydrogen cyanide was taken up in 2000 ml methanol. The resulting solution was reacted with 150 ml concentrated aqueous hydrochloric acid and treated with gaseous hydrogen chloride. The temperature of the solution at first amounted to 15° C but was increased in a short time to about 65° C so that the solution was brought to boiling. The solution was then allowed to stand for 5 hours under stirring. The 2-isopropyl-5,5-dimethyl-thiazolidine-4-carbonamide-hydrochloride separated out as crystals. The crystals were filtered off and washed with acetone. By evaporating the mother liquor, a further portion of the carbonamide-hydrochloride was recovered. This was also washed with acetone. The total yield of carbonamide-hydrochloride amounted to 1035 g. Referred to the charged thiazoline, this corresponded to a yield of 90%. The carbonamide-hydrochloride had a melting point (decomposition point) of 240°–242° C.

214 g (0.9 mol) Of 2-isopropyl-5,5-dimethyl-thiazolidine-4-carbonamide-hydrochloride were dissolved in a mixture of 100 ml water with 300 ml concentrated hydrochloric acid and this solution maintained under reflux at the boiling temperature (105° C) for 40 hours. The main portion of the reaction product was separated out of the solution on cooling. The separated product was filtered off and the filtrate evaporated to dryness under reduced pressure. The crude product thereby recovered was purified by washing with 300 ml acetone. The thusly decolored substance contained about 45 g ammonium chloride, 201 g 2-isopropyl-5,5-dimethyl-thiazolidine-4-carboxylic acid-hydrochloride corresponding to a 93% yield calculated on the charged carbonamide-hydrochloride and had a melting point (decomposition point) of 211°–213° C. The further working up to form penicillamine was carried out in the usual manner.

EXAMPLE 10

2-Isopropyl-5,5-dimethyl-thiazolidine-4-carbonitrile prepared by reacting 787 g (5 mol) 2-isopropyl-5,5-dimethylthiazoline-$\Delta^3$ with 438 g (10 mol) hydrogen cyanide in the conventional manner was taken up to 2500 methanol. The solution following the addition thereto of 150 ml concentrated hydrochloric acid was treated with gaseous hydrogen chloride for 3 days. The temperature was maintained for the first 6 hours under cooling at 5° C. Thereafter in the further course of the reaction without cooling the temperature increased to 35°–45° C. The thiazolidine-4-carbonamide-hydrochloride which separated out was filtered off and the filtrate evaporated to dryness under reduced pressure. The residue was washed with 1000 ml acetone. There were recovered a total of 1063 g 2-isopropyl-5,5-dimethyl-thiazolidine-4-carbonamide-hydrochloride corresponding to a yield of 80% calculated on the charged thiazoline. The carbonamide-hydrochloride had a melting point (decomposition point) of 240°–242° C.

239 g (1 mol) of the thusly recovered 2-isopropyl-5,5-dimethyl-thiazolidine-4-carbonamide-hydrochloride was taken up in a mixture of 500 ml concentrated aqueous hydrogen chloride and 1000 ml of water. The solution was kept for 4 hours at the boiling temperature (about 105° C), then cooled and evaporated to dryness under reduced pressure. The product contained 214 g 2-isopropyl-5,5 dimethyl-thiazolidine-4-carboxylic acid-hydrochloride corresponding to a 89% yield calculated on the charged carbonamide-hydrochloride. IR-spectroscopic analysis of the product showed no carbonamide-hydrochloride. The further working up to penicillamine was carried out in the conventional manner.

What is claimed is:

1. In a process for the production of D,L-penicillamine by the reaction of isobutyraldehyde with sulfur and ammonia to form 2-isopropyl-5,5-dimethylthiazoline-3, conversion of the thiazoline with anhydrous hydrogen cyanide into 2-isopropyl-5,5-dimethyl-thiazolidine-4-carbonitrile, hydrolysis of the nitrile with hydrochloric acid to 2-isopropyl-5,5-dimethylthiazolidine-4-carboxylic acid hydrochloride and ammonium chloride, working up the mixture and separation of the ammonium chloride and hydrolytically breaking down the 2-isopropyl-5,5-dimethylthiazolidine-4-carboxylic acid to form penicillamine the improvement comprising carrying out the hydrolysis of the 2-isopropyl-5,5-dimethylthiazolidine-4-carbonitrile by (1) converting the 2-isopropyl-5,5-dimethylthiazolidine-4-carbonitrile with the hydrochloric acid into 2-isopropyl-5,5-dimethylthiazolidine-4-carbonamide hydrochloride at a temperature of 0° to 80° C and (2) converting the 2-isopropyl-5,5-dimethylthiazolidine-4-carbonamide hydrochloride into 2-isopropyl-5,5-dimethylthiazolidine-4-carboxylic acid hydrochloride at a temperature of 80° to 150° C.

2. The process of claim 1 wherein step (1) is carried out at a temperature of 0° to 50° C.

3. A process according to claim 2 wherein step (2) is carried out at a temperature of 100° to 105° C.

4. A process according to claim 3 wherein there is used 10 to 15% aqueous hydrochloric acid in step (2).

5. A process according to claim 1 wherein step (1) is begun at a temperature of 0° to 20° C.

6. A process according to claim 5 wherein during step (1) the hydrolysis temperature is increased to 50 to 65° C.

7. A process according to claim 5 wherein step (2) is carried out at a temperature of 100° to 105° C.

8. A process according to claim 7 wherein there is used 10 to 15% aqueous hydrochloric acid in step (2).

9. A process according to claim 1 wherein the temperature in step (2) is 100° to 105° C.

10. A process according to claim 9 wherein there is used 10 to 15% aqueous hydrochloric acid in step (2).

11. A process according to claim 1 wherein there is used 10 to 15% aqueous hydrochloric acid in step (2).

12. A process according to claim 1 wherein step (1) is carried out in water or a lower alkanol.

13. A process according to claim 12 wherein the hydrolysis in step (1) is carried out with addition of gaseous hydrogen chloride.

14. A process according to claim 12 wherein the hydrolysis in step (1) is carried out at a temperature of 50° to 65° C.

* * * * *